US007187966B2

(12) United States Patent
Kaiser et al.

(10) Patent No.: US 7,187,966 B2
(45) Date of Patent: Mar. 6, 2007

(54) METHOD AND APPARATUS FOR DISPLAYING ALTERNANS DATA

(75) Inventors: Willi Kaiser, Emmendingen (DE); Martin Findeis, Freiburg (DE)

(73) Assignee: Ge Medical Systems Information Technologies, Inc., Milwaukee, WI (US)

( * ) Notice: Subject to any disclaimer, the term of this patent is extended or adjusted under 35 U.S.C. 154(b) by 219 days.

(21) Appl. No.: 10/824,987

(22) Filed: Apr. 15, 2004

(65) Prior Publication Data

US 2005/0234362 A1 Oct. 20, 2005

(51) Int. Cl.
*A61B 5/0402* (2006.01)

(52) U.S. Cl. .................. 600/515; 600/509; 600/523; 345/440

(58) Field of Classification Search ............... 600/509, 600/512, 515, 517, 523, 525, 516; 345/440
See application file for complete search history.

(56) References Cited

U.S. PATENT DOCUMENTS

| | | | |
|---|---|---|---|
| 3,554,187 A | 1/1971 | Glassner et al. | |
| 3,658,055 A | 4/1972 | Abe et al. | |
| 3,759,248 A | 9/1973 | Valiquette | |
| 3,821,948 A | 7/1974 | King | |
| 3,902,479 A | 9/1975 | Chaumet | |
| 3,952,731 A | 4/1976 | Worstencroft | |
| 4,124,894 A | 11/1978 | Vick et al. | |
| 4,136,690 A | 1/1979 | Anderson et al. | |
| 4,170,992 A | 10/1979 | Dillman | |
| 4,181,135 A | 1/1980 | Andresen et al. | |
| 4,202,340 A | 5/1980 | Langer et al. | |
| 4,316,249 A | 2/1982 | Gallant et al. | |
| 4,417,306 A | 11/1983 | Citron et al. | |
| 4,422,459 A | 12/1983 | Simson | |
| 4,432,375 A | 2/1984 | Angel et al. | |

(Continued)

FOREIGN PATENT DOCUMENTS

| | | |
|---|---|---|
| DE | 2604460 | 8/1977 |
| DE | 3303104 | 8/1984 |
| DE | 4024360 | 3/1991 |
| EP | 0080821 | 6/1983 |
| FR | 2539978 | 8/1984 |
| GB | 2070871 | 9/1981 |
| WO | WO81/02832 | 10/1981 |

OTHER PUBLICATIONS

Achim Michael Nuebling, U.S. Appl. No. 09/711,691, filed Nov. 13, 2000.

(Continued)

*Primary Examiner*—Robert Pezzuto
*Assistant Examiner*—Shevon Johnson
(74) *Attorney, Agent, or Firm*—Andrus, Sceales, Starke & Sawall, LLP (57) ABSTRACT

Method and apparatus for displaying alternans data of an electrocardiogram signal having a plurality of odd beats and a plurality of even beats. The method can include calculating an odd median complex for at least one of the plurality of odd beats, the odd median complex having a plurality of odd data points; calculating an even median complex for at least one of the plurality of even beats, the even median complex having a plurality of even data points; comparing the plurality of odd data points with the plurality of even data points to generate a plurality of difference data points; assigning each one of the plurality of difference data points a color corresponding to an amplitude; displaying the plurality of difference data points as a difference curve; and displaying a plurality of difference curves in a temporal alignment.

29 Claims, 4 Drawing Sheets

U.S. PATENT DOCUMENTS

| | | |
|---|---|---|
| 4,457,315 A | 7/1984 | Bennish |
| 4,458,691 A | 7/1984 | Netravali |
| 4,458,692 A | 7/1984 | Simson |
| 4,475,558 A | 10/1984 | Brock |
| 4,492,235 A | 1/1985 | Sitrick |
| 4,519,395 A | 5/1985 | Hrushesky |
| 4,583,553 A | 4/1986 | Shah et al. |
| 4,589,420 A | 5/1986 | Adams et al. |
| 4,603,703 A | 8/1986 | McGill et al. |
| 4,616,659 A | 10/1986 | Prezas et al. |
| 4,665,485 A | 5/1987 | Lundy et al. |
| 4,679,144 A | 7/1987 | Cox et al. |
| 4,680,708 A | 7/1987 | Ambos et al. |
| 4,732,157 A | 3/1988 | Kaplan et al. |
| 4,796,638 A | 1/1989 | Sasaki |
| 4,802,491 A | 2/1989 | Cohen et al. |
| 4,832,038 A | 5/1989 | Arai et al. |
| 4,854,327 A | 8/1989 | Kunig |
| 4,860,762 A | 8/1989 | Heumann et al. |
| 4,896,677 A | 1/1990 | Kaneko et al. |
| 4,924,875 A | 5/1990 | Chamoun |
| 4,928,690 A | 5/1990 | Heilman et al. |
| 4,938,228 A | 7/1990 | Righter et al. |
| 4,951,680 A | 8/1990 | Kirk et al. |
| 4,955,382 A | 9/1990 | Franz et al. |
| 4,958,641 A | 9/1990 | Digby et al. |
| 4,972,834 A | 11/1990 | Begemann et al. |
| 4,974,162 A | 11/1990 | Siegel et al. |
| 4,974,598 A | 12/1990 | John |
| 4,977,899 A | 12/1990 | Digby et al. |
| 4,979,510 A | 12/1990 | Franz et al. |
| 4,989,610 A | 2/1991 | Patton et al. |
| 5,000,189 A | 3/1991 | Throne et al. |
| 5,010,888 A | 4/1991 | Jadvar et al. |
| 5,020,540 A | 6/1991 | Chamoun |
| 5,025,795 A | 6/1991 | Kunig |
| 5,042,497 A | 8/1991 | Shapland |
| 5,092,341 A | 3/1992 | Kelen |
| 5,109,862 A | 5/1992 | Kelen et al. |
| 5,117,833 A | 6/1992 | Albert et al. |
| 5,117,834 A | 6/1992 | Kroll et al. |
| 5,148,812 A | 9/1992 | Verrier et al. |
| 5,188,116 A | 2/1993 | Pommrehn et al. |
| 5,201,321 A | 4/1993 | Fulton |
| 5,234,404 A | 8/1993 | Tuttle et al. |
| 5,253,650 A | 10/1993 | Wada |
| 5,265,617 A | 11/1993 | Verrier et al. |
| 5,277,190 A | 1/1994 | Moulton |
| 5,323,783 A | 6/1994 | Henkin et al. |
| 5,343,870 A | 9/1994 | Gallant et al. |
| 5,361,776 A | 11/1994 | Samuelson et al. |
| 5,423,878 A | 6/1995 | Franz |
| 5,437,285 A | 8/1995 | Verrier et al. |
| 5,560,370 A | 10/1996 | Verrier et al. |
| 5,570,696 A | 11/1996 | Arnold et al. |
| 5,819,741 A | 10/1998 | Karlsson et al. |
| 5,827,195 A | 10/1998 | Lander |
| 5,921,940 A | 7/1999 | Verrier et al. |
| 5,935,082 A | 8/1999 | Albrecht et al. |
| 6,169,919 B1 | 1/2001 | Nearing et al. |
| 6,409,659 B1 | 6/2002 | Warner et al. |
| 6,453,191 B2 | 9/2002 | Krishnamachari |
| 6,668,189 B2 | 12/2003 | Kaiser et al. |
| 6,823,213 B1 * | 11/2004 | Norris et al. .................. 607/9 |
| 6,967,652 B1 * | 11/2005 | Nubling et al. ............. 345/440 |

OTHER PUBLICATIONS

Speranza et al., 'Beat-to-beat measurement and analysis of the R-T interval in 24 h ECG Holter recordings,' Med and Biol Eng & Comput, 1993, 31, pp. 487-494.

Narayanaswamy et al., 'Selective beat signal averaging and spectral analysis of beat intervals to determine the mechanisms of premature ventricular contractions,' University of Oklahoma Health Sciences Center, May 1993, pp. 81-84.

Laks et al., 'ECG computer program developed for a retrospective and prospective study of the Pardee T wave,' Department of Medicine, UCLA School of Medicine, Harbor-UCLA Medical Center, Torrence, CA, 1992, pp. 365-368.

Makarov et al., 'Holter monitoring in the long QT syndrome of children and adolescents,' Cor Vasa, 1990, 32(6), pp. 474-483.

Navarro-Lopez et al., 'Isolated T wave alternans elicited by hypocalcemia in dogs,' Electrocardiology, 1978, 11(2), pp. 103-108.

Little et al., 'Torsade de Pointes and T-U wave alternans associated with arsenic poisoning,' Pace, 1990, 13, pp. 164-170.

Weintraub et al., 'The congenital long QT syndromes in childhood,' Journal of the American College of Cardiology, Sep. 1990, 16(3), pp. 674-680.

Bibler et al., 'Recurrent ventricular tachycardia due to pentamidine-induced cardiotoxicity,' Chest, Dec. 1988, 94(6), pp. 1303-1306.

Ahnve et al., 'Circadian variations in cardiovascular parameters during sleep deprivation, A noninvasive study of young healthy men,' European Journal of Applied Physiology, 1981, 46, pp. 9-19.

Surawicz, 'ST-segment, T-wave, and U-wave changes during myocardial ischmeia and after myocardial infarction,' Canadian Journal of Cardiology, Supplement A, Jul. 1986, pp. 71A-84A.

Stroobandt et al., 'Simultaneous recording of atrial and ventricular monophasic action potentials: monophasic action potential duration during atrial pacing, ventricular pacing, and ventricular fibrillation,' Pace, Jul.-Aug. 1985, 8, pp. 502-511.

Sharma et al., 'Romano-Ward prolonged QT syndrome with intermittant T wave alternans and atrioventricular block,' American Heart Journal, 1981, pp. 500-501.

Navarro-Lopez et al., 'Isolated T wave alternans,' American Heart Journal, 1978, pp. 369-374.

Mitsutake et al., 'Usefulness of the Valsalva Maneuver in management of the long QT syndrome,' Circulation, 1981, 63(5), pp. 1029-1035.

Nearing et al., 'Personal computer system for tracking cardiac vulnerability by complex demodulation of the T wave,' American Physiological Society, 1993, pp. 2606-2612.

Joyal et al., 'ST-segment alternans during percutaneous transluminal coronary angioplasty,' Division of Cardiology, Department of Medicine, University of Florida and the Veterans Administration Medical Center, Jun. 1984, pp. 915-916.

Schwartz et al., 'Electrical alternation of the T-wave: clinical and experimental evidence of its relationship with the sympathetic nervous system and with the long Q-T syndrome,' American Heart Journal, Jan. 1975, 89(1), pp. 45-50.

Schwartz, 'Idiopathic long QT syndrome: progress and questions,' American Heart Journal, Feb. 1985, 109(2), pp. 399-411.

Verrier et al., 'Electrophysiologic basis for T wave alternans as an index of vulnerability to ventricular fibrillation,' Journal of Cardiovascular Electrophysiology, May 1994, 5(5), pp. 445-461.

Verrier et al., 'Behavioral states and sudden cardiac death,' Pace, Sep. 1992, 15, pp. 1387-1393.

Turitto et al., 'Alternans of the ST segment in variant angina,' Chest, Mar. 1988, 93(3), pp. 587-591.

Ring et al., 'Exercise-induced ST segment alternans,' American Heart Journal, May 1986, 111(5), pp. 1009-1011.

Wayne et al., 'Exercise-induced ST segment alternans,' Chest, May 1983, 83(5), pp. 824-825.

Verrier et al., 'Ambulatory electrocardiogram-based tracking of T wave alternans in postmyocardial infarction patients to assess risk of cardiac arrest or arrhythmic death,' Journal of Cardiovascular Electrophysiology, Jul. 2003, 14(7), pp. 705-711.

* cited by examiner

METHOD AND APPARATUS FOR DISPLAYING ALTERNANS DATA

BACKGROUND OF THE INVENTION

The present invention relates to displaying cardiological data, and more specifically to methods and apparatus for displaying alternans data of an electrocardiogram ("ECG") signal.

Alternans are subtle beat-to-beat changes in the repeating pattern of an ECG signal. Several studies have demonstrated a high correlation between an individual's susceptibility to ventricular arrhythmias and sudden cardiac death and the presence of a T-wave alternans ("TWA") pattern of variation in the individual's ECG signal.

While an ECG signal typically has an amplitude measured in millivolts, an alternans pattern of variation with an amplitude on the order of a microvolt may be clinically significant. Accordingly, an alternans pattern of variation is typically difficult and time consuming to detect by visual inspection of the ECG signal. Instead, electronic detection and quantification of the alternans pattern of variation is necessary. Such electronic detection and quantification of the alternans pattern of variation is complicated by the presence of noise in the ECG signal. Noise may result in beat-to-beat variations that have a larger magnitude than the alternans pattern of variation.

Current techniques used to quantify patterns of variation in alternans data compensate for at least some of the noise in the ECG signal. However, artifacts resulting from a patient's movement (e.g., pedaling, footfalls, and the like) and/or respiration during exercise or Holter testing may nevertheless interfere with a clinician's assessment of the patterns of variation in the alternans data. These artifacts often overlay the patterns of variation in the alternans data.

BRIEF DESCRIPTION OF THE INVENTION

In light of the above, a need exists for an improved method of displaying alternans data so that a clinician can observe patterns of variation and/or trends in the alternans data and assess the quality of the alternans data.

Accordingly, one embodiment of the invention provides a method of displaying alternans data of an electrocardiogram signal, the electrocardiogram signal having odd beats and even beats. The method can include calculating an odd median complex for the odd beats, the odd median complex having odd data points; calculating an even median complex for the even beats, the even median complex having even data points; comparing the odd data points with the even data points to generate difference data points; assigning each one of the difference data points a color corresponding to an amplitude; displaying the difference data points as a difference curve; and displaying two or more difference curves in a temporal alignment. In some embodiments, the difference data points can be assigned a shade of gray or a true color. The difference curves can be displayed as a three-dimensional representation in some embodiments, and as a two-dimensional representation in other embodiments.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Figure 1:
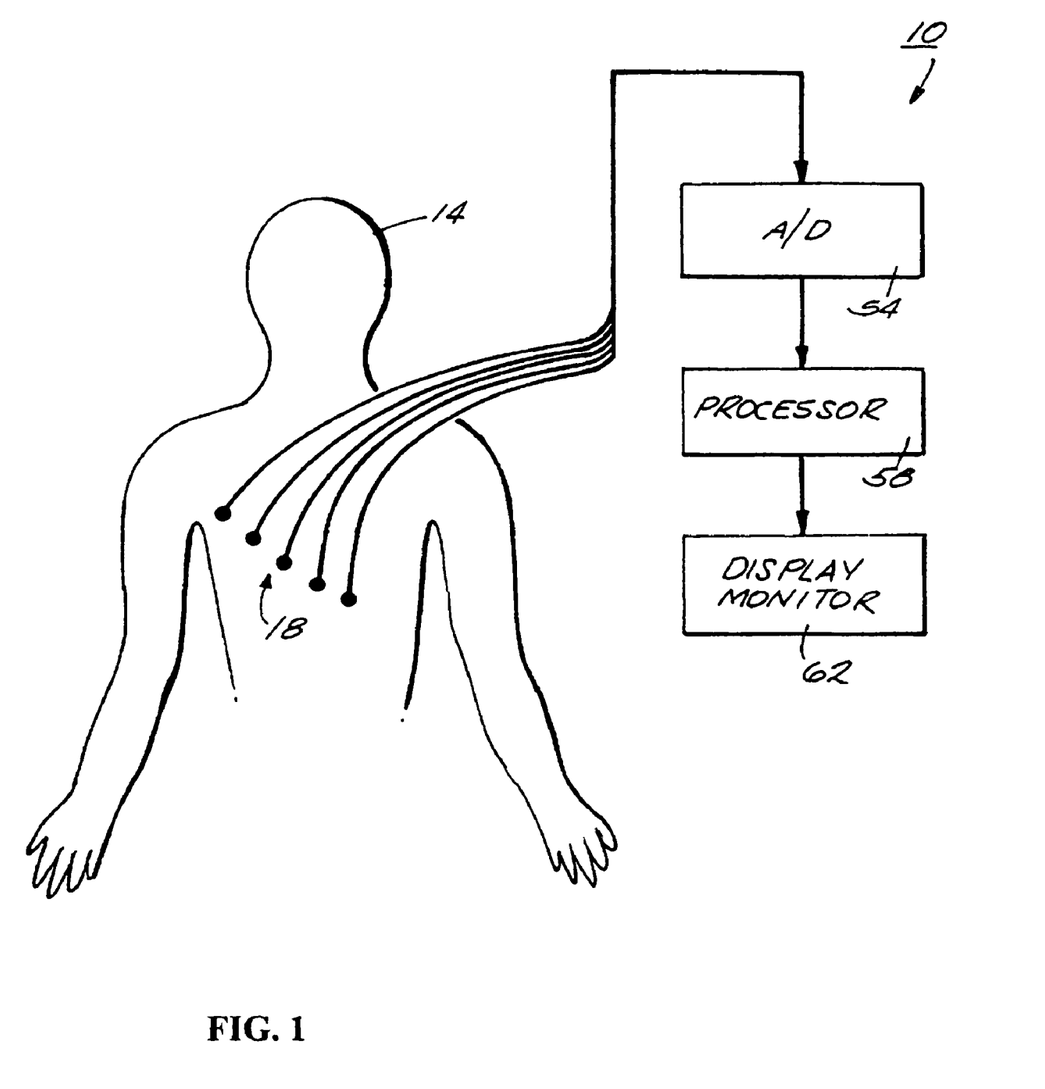
FIG. 1 is a block diagram illustrating a patient monitoring system embodying the invention.

FIG. 1 illustrates a patient monitoring system 10 according to one embodiment of the invention. The patient monitoring system 10 can acquire and process ECG data and can display alternans data generated from the ECG data. Hereinafter, the term "alternans data" shall be broadly defined as including T-wave alternans data or any other type of alternans data that is capable of being displayed. The monitoring system 10 can be coupled to the patient 14 by one or more sensors or transducers which can include, for example, electrodes 18 mounted on the patient's chest for obtaining an ECG signal and a heart rate. The terms "sensor" and "transducer" as used herein refer to any device capable of generating an electrical output signal from a mechanical, chemical, or electrical input.

The ECG signals acquired with the electrodes 18 can be converted from analog form to digital form by an analog to digital converter 54 and can then be provided to a processor 58 that can generate alternans data from the ECG data. The alternans data can be displayed on a monitor 62. The monitor 62 can be a conventional computer-style display monitor having a cathode ray tube ("CRT"). The CRT can include a plurality of pixels. As is known in the art, each pixel can be energized electronically so that the pixel emits light visible to a user of the monitoring system 10. In one embodiment, the monitor 62 can include a black and white display capable of showing black, white and a plurality of gray shades (e.g., 64 gray shades or more) between black and white. In another embodiment, the monitor 62 can include a color display (e.g., a red-blue-green color display) capable of displaying a plurality of colors (e.g., 256 colors or more). The term "color" as used herein and in the appended claims refers to either true colors or shades of gray in combination with white and black, unless the context indicates otherwise. In other embodiments, the data can be displayed on other types of displays including liquid-crystal displays, plasma screens, holographic displays, and the like (each of which may be capable of displaying hundreds or thousands of colors).

Although any alternans data of an ECG signal can be displayed using the invention, the embodiments of the invention discussed below are in the context of displaying TWA data of an ECG signal. In some embodiments, the TWA data can be obtained using the systems and methods as described in U.S. Pat. No. 6,169,919 entitled "System and Method for Quantifying Alternation in an Electrocardiogram Signal." However, ECG data representing a digitized ECG signal and the corresponding TWA data can be obtained in any suitable manner. In some embodiments, the ECG data can be used to continuously calculate odd and even median beat complexes. A median complex can be an incremental time-average representation of a series of beats. With each new odd beat, an odd median complex for the odd beats in the ECG data can be updated. Similarly, with each new even beat, an even median complex for the even beats in the ECG data can be updated. Values of the current odd and even median complexes can be stored cyclically (e.g., every fifteen seconds) as an odd and even median complex pair. The odd and even median complex pairs can be compared to obtain an estimate of the amplitude of beat-to-beat alternation in the ECG signal. The ECG data can be filtered prior to calculation of the even and odd median complexes. In one embodiment, filtering of the ECG data can involve low-pass filtering the ECG data to remove high frequency noise, applying a baseline wander removal filter to the ECG data to remove low frequency artifacts, removing arrhythmic beats from the ECG data, and eliminating noisy beats from the ECG data. The filtered data is generally more suitable for calculation of an accurate estimate of alternation.

Although the filtering produces fairly high quality alternans data, elimination of all artifact has not been realized by conventional systems. As a result, it is difficult for a clinician to assess whether the variability in the alternans data is due to alternation of the ECG signal, noise in the ECG signal, or a combination thereof. Accordingly, in some embodiments of the invention, the display of alternans data in a temporal alignment allows for the assessment of trends in the alternans data. The assessment of trends of alternans data according to some embodiments of the invention can include distinguishing between alternans distribution and artifact distribution. As discussed further below, the alternans distribution can be displayed in a smooth and clear fashion while the artifact distribution can be displayed in a fuzzy fashion. If the assessment determines that artifacts are present in the alternans data, in some embodiments, the algorithm utilized to generate the alternans data can be manually corrected to filter out at least some of the artifact. In other embodiments, values generated using the algorithm can be manually overwritten using a text editor.

The processor 58 can calculate a difference curve for each stored odd and even median complex by sampling a number of corresponding data points of each median complex and determining the difference. In the embodiments illustrated in FIGS. 2–7, the difference curve is an absolute difference curve. Every data point of the absolute difference curve can represent an amplitude value. The amplitude value can be calculated as an absolute value of the difference between the corresponding data points of the odd and even median complexes of an odd and even median complex pair. Utilization of an absolute difference can provide similar results regardless if the first beat is taken as an odd beat or as an even beat.

The data points representing the absolute difference curves can be stored in a memory array (e.g., a waveform array). In one embodiment, consecutive absolute difference curves can be displayed in a temporal alignment as a three-dimensional representation. In another embodiment, consecutive absolute difference curves can be displayed in a temporal alignment as a two-dimensional representation. For example, a first set of alternans data is shown displayed in FIG. 2 as a three-dimensional representation and in FIG. 3 as a two-dimensional representation. Similarly, a second set of alternans data is shown displayed in FIG. 4 as a three-dimensional representation and in FIG. 5 as a two-dimensional representation. In addition, a third set of alternans data is shown displayed in FIG. 6 as a three-dimensional representation and in FIG. 7 as a two-dimensional representation. Each set of alternans data can include a plurality of absolute difference curves displayed in a chronological order. With reference to FIGS. 2–7, an indicator positioned at approximately sample number 250 can represent the QRS-end of each beat of the ECG signal, and an indicator positioned at approximately sample number 320 can represent the T-end of each beat of the ECG signal. Such indicators can provide a reference for determining the ST-segment and the T-wave portion of the ECG signal. In other embodiments, alternative indicators can be utilized in the representations of the alternans data.

Figure 2:
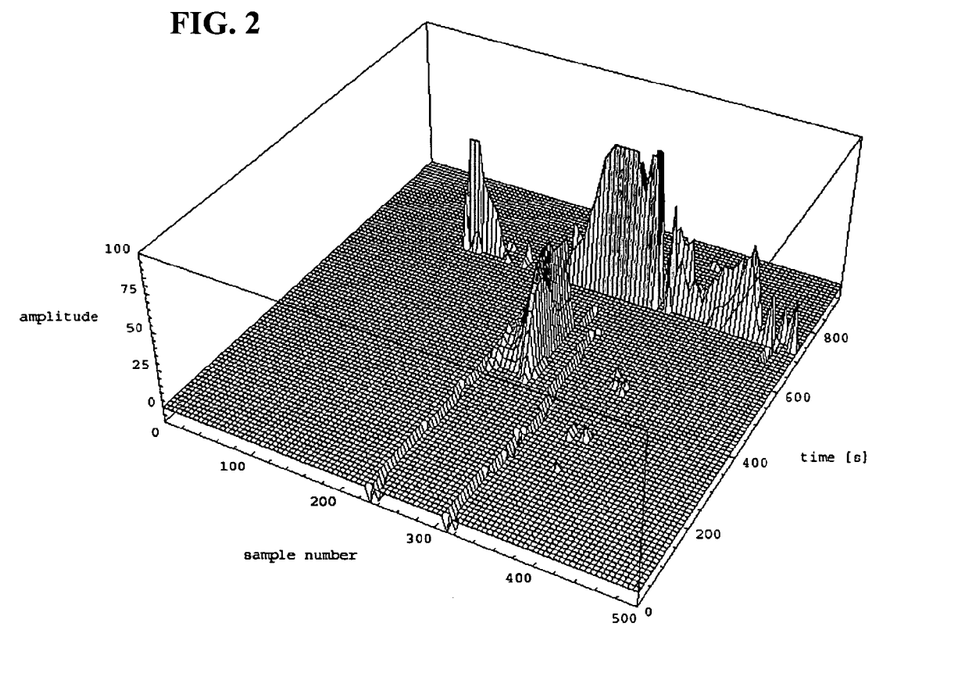
FIG. 2 is an example of a three-dimensional representation of a first set of alternans data from an ECG signal generated by the patient monitoring system of FIG. 1.
Figure 3:
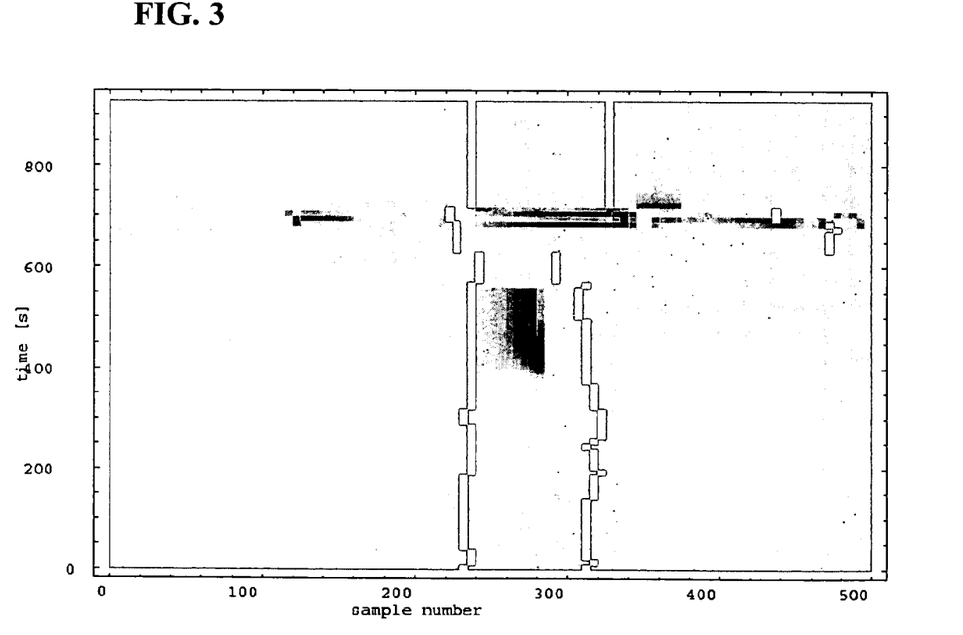
FIG. 3 is an example of a two-dimensional representation of the alternans data of FIG. 2.

As shown in FIGS. 2 and 3, the first set of data can include an alternans distribution at approximately 500 seconds and an artifact distribution at approximately 700 seconds. The alternans distribution can be positioned between the QRS-end and T-end indicators and can include a smooth and clear appearance. The artifact distribution can extend outside the T-wave portion and can include a fuzzy or cliff-like type appearance.

Figure 4:
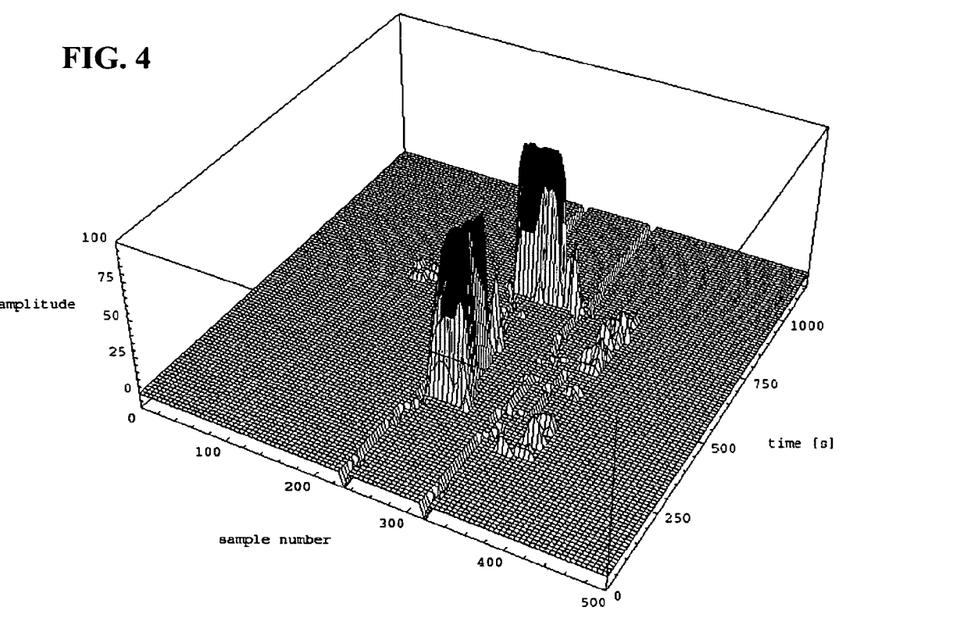
FIG. 4 is an example of a three-dimensional representation of a second set of alternans data from an ECG signal generated by the patient monitoring system of FIG. 1.
Figure 5:
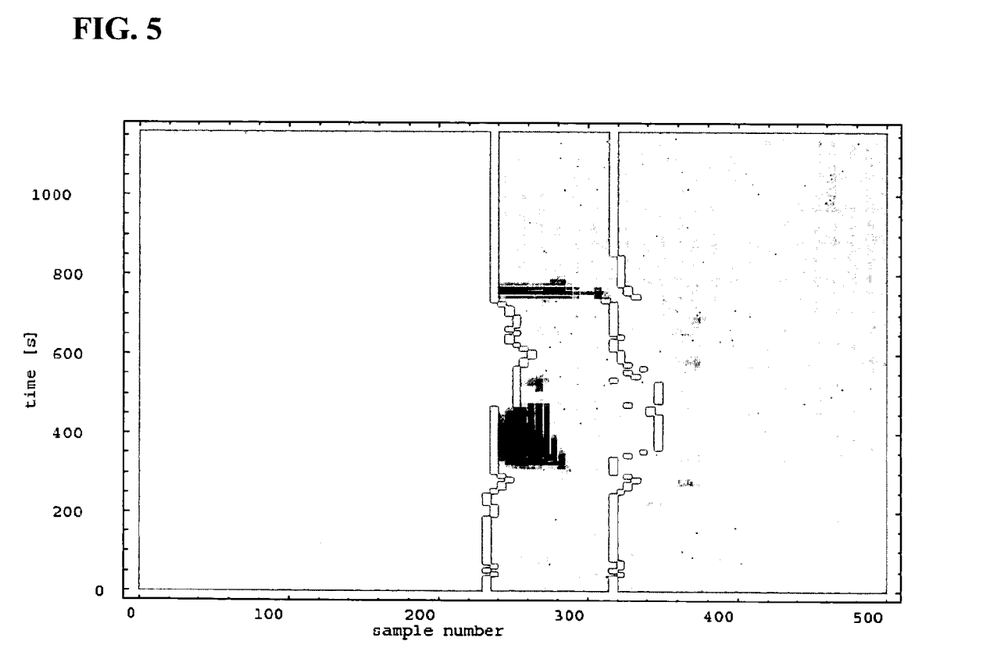
FIG. 5 is an example of a two-dimensional representation of the second set of alternans data of FIG. 4.

As shown in FIGS. 4 and 5, the second set of data can include a first alternans distribution at approximately 450 seconds and a second alternans distribution at approximately 800 seconds. Each alternans distribution can be positioned between the QRS-end and T-end indicators and can include a smooth and clear appearance.

Figure 6:
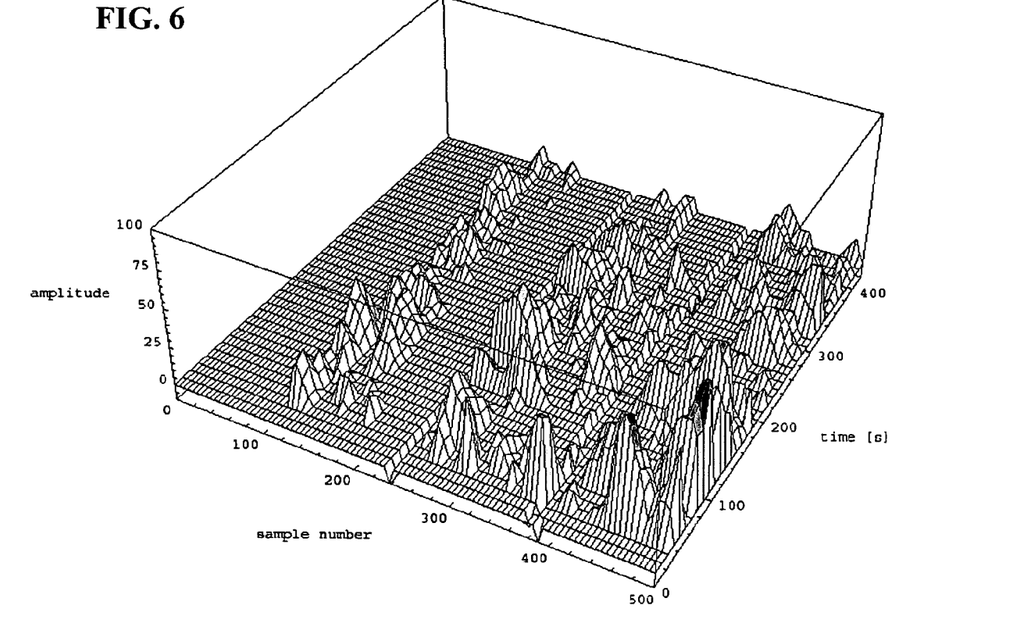
FIG. 6 is an example of a three-dimensional representation of a third set of alternans data from an ECG signal generated by the patient monitoring system of FIG. 1.
Figure 7:
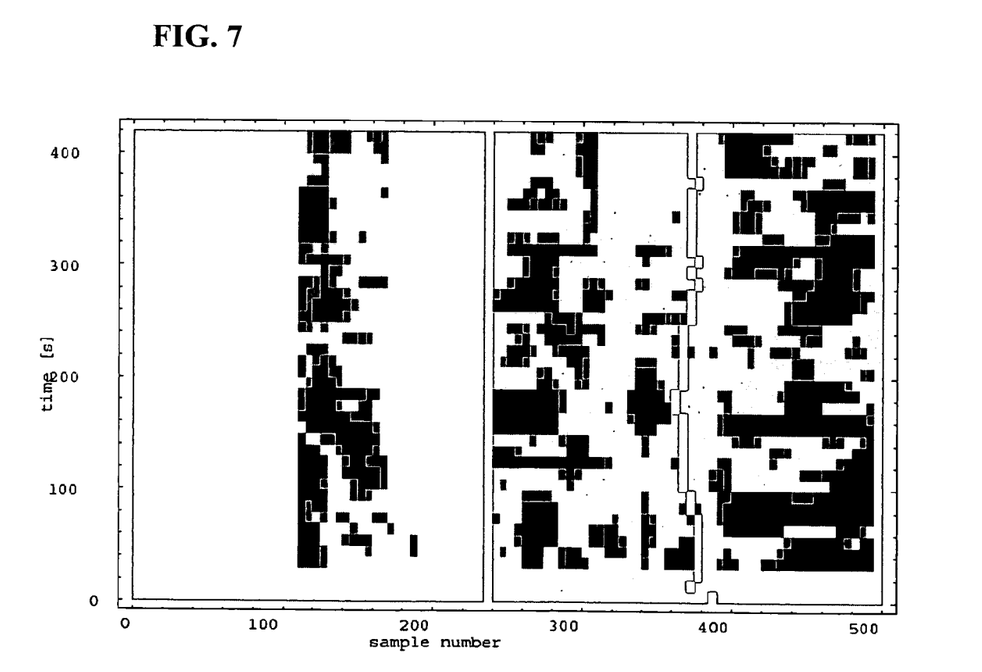
FIG. 7 is an example of a two-dimensional representation of the third set of alternans data of FIG. 6.

As shown in FIGS. 6 and 7, the third set of data can include a false-positive alternans distribution (i.e., an artifact distribution). According to one embodiment of the invention, the false-positive alternans distribution can have a maximum amplitude of approximately 50 microvolts, can extend outside the T-wave portion, and can include a fuzzy or cliff-like type appearance.

In one embodiment, a catalog of representative displays of alternans data including alternans distributions and/or artifact distributions can be provided with the patient monitoring system 10. The catalog can be used to train clinicians to assess the quality of the alternans data displayed and further to determine when correction of the alternans quantification algorithm is required.

In some embodiments, for the display of alternans data as a three-dimensional representation, the absolute difference curves stored in the waveform array can be processed by a software routine stored in the processor 58 and can be displayed on the display monitor 62 in a quasi-three-dimensional color display. The display can include X, Y, and Z axes where the X-axis coordinate can represent the sample number of a given absolute difference curve, the Y-axis coordinate can represent the time or the chronology of the absolute difference curves (i.e., when the respective odd and even median complex pair used to determine the absolute difference curve was obtained relative to the starting point), and the Z-axis coordinate can represent the amplitude of the data points of the absolute difference curves. However, any one of the X, Y, and Z axes can represent any one of the sample number, the time, and the amplitude of the data points. A change in the axes representation merely alters the orientation of the display.

In one embodiment for a three-dimensional representation, the processor 58 can set the current waveform count to the first waveform in the waveform array that is to be displayed. The processor 58 can initialize a Y-coordinate value to Y=0 on the display, can set a sample pointer to the first data sample in the current absolute difference curve, and can initialize an X-coordinate value to X=0 on the display. The processor 58 can retrieve the current data point from the current absolute difference curve and can read the amplitude of the data point. The processor 58 can generate a first variable corresponding to the current data point (e.g., X=0, Y=0, and Z=amplitude value of first data point), can increment the X-coordinate value to read the next data point, can read the amplitude of that next data point, and can generate a second variable corresponding to the incremented data point (e.g., X=1, Y=0, and Z=amplitude value of incremented data point). This process can continue until each data point has been analyzed.

The processor 58 can increment the current waveform count to the second waveform in the waveform array. The data points of the incremented waveform can be similarly analyzed. In some embodiments, the processor 58 can draw a quadrilateral around the corresponding first and second variables of the first and second waveforms. The quadrilateral can be dissected by establishing a line between the first variable of the current waveform and the corresponding second variable of the previous waveform, resulting in two triangles. The processor 58 can determine a color for each triangle and the triangles can be colored based on the amplitude value of a respective point of the triangle. This process can continue until each waveform has been displayed.

As shown in FIGS. 2, 4, and 6, successive absolute difference curves can be plotted in a stacked colorized representation (whether in true colors or in shades of gray as shown in FIGS. 2, 4, and 6) to provide a perspective or representative three-dimensional view of the alternans data over an extended period of time. This presentation can highlight trends that may exist in the alternans data. In some embodiments, the representative three-dimensional view of the alternans data can be rotated by the processor 58 so that it can be viewed by a clinician from different perspectives. The processor 58 can rotate the representative three-dimensional image by rotating the X, Y, and Z axes. As the image rotates, the clinician can more easily characterize different segments of the alternans data. In one embodiment, the clinician can rotate the image 360 degrees in order to view each side of the image. The use of color to enhance this display can allow easier detection by the clinician of significant aspects of the data.

For the display of alternans data as a two-dimensional representation, the absolute difference curves stored in the waveform array can be processed by a software routine stored in the processor 58 and can be displayed on the monitor 62 in a two-dimensional color display. The display can include X and Y axes, where the X-axis coordinate represents the sample number of a given absolute difference curve, and the Y-axis coordinate represents the time or the chronology. The amplitude of the data point can be represented by the color of the pixel representing each data point. Accordingly, the alternans data can be displayed as a type of color density diagram.

In one embodiment for a two-dimensional representation, the software program can scale the Z-coordinate values of the three-dimensional representation to zero to obtain a two-dimensional representation. In another embodiment for a two-dimensional representation, the software program can generate only X and Y coordinate values. For such an embodiment, the processor 58 can set the current waveform count to the first waveform in the waveform array that is to be displayed. The processor 58 can initialize a Y-coordinate value to Y=0 on the display, can set a sample pointer to the first data sample in the current waveform, and can initialize an X-coordinate value to X=0 on the display. The processor 58 can retrieve the current data point from the current absolute difference curve, can determine a pixel color for the data point based on the amplitude of the waveform data point, and can plot that data point at the respective X and Y coordinate using the selected color. The processor 58 can increment the X-coordinate value and can repeat the process for each data point in the current waveform until all data points in that waveform have been plotted. Once all data points in that waveform are plotted, the processor 58 can increment the Y-coordinate in order to retrieve the next waveform in the waveform array. This process can be repeated until all of the waveforms in the waveform array are plotted. The results can be displayed as shown in FIGS. 3, 5, and 7. This presentation can also highlight trends that may exist in the alternans data.

In some embodiments, the color scheme of the monitoring system 10 can be at least partially configurable. That is, the clinician can select a color to represent a given amplitude. Alternatively, the monitoring system 10 can be programmed to provide the clinician with a set of manufacturer-defined color schemes. The display can include graphical and/or numerical information to indicate the corresponding value for each color used. Alternatively, the absolute difference curves can be displayed in other embodiments of the invention.

Various features and advantages of the invention are set forth in the following claims.

The invention claimed is:

1. A method of displaying alternans data of an electrocardiogram signal, the electrocardiogram signal having a plurality of odd beats and a plurality of even beats, the method comprising:

calculating an odd median complex for at least one of the plurality of odd beats, the odd median complex having a plurality of odd data points;

calculating an even median complex for at least one of the plurality of even beats, the even median complex having a plurality of even data points;

comparing the plurality of odd data points with the plurality of even data points to generate a plurality of difference data points;

assigning each one of the plurality of difference data points a color corresponding to an amplitude;

displaying the plurality of difference data points as a difference curve; and generating a plurality of difference curves and displaying the plurality of difference curves in a temporal alignment.

2. A method as set forth in claim 1 and further comprising generating a plurality of absolute difference data points.

3. A method as set forth in claim 1 and further comprising distinguishing between alternans distribution and artifact distribution.

4. A method as set forth in claim 1 and further comprising displaying the plurality of difference curves in a temporal alignment as a two-dimensional representation.

5. A method as set forth in claim 1 and further comprising displaying the plurality of difference curves in a temporal alignment as a three-dimensional representation.

6. A method as set forth in claim 1 and further comprising assigning a true color to each one of the plurality of difference data points.

7. A method as set forth in claim 1 and further comprising assigning a shade of gray to each one of the plurality of difference data points.

8. A method as set forth in claim 1 and further comprising assigning to each one of the plurality of difference data points X and Y coordinates and plotting each one of the plurality of difference data points to produce a two-dimensional representation.

9. A method as set forth in claim 1 and further comprising assigning to each one of the plurality of difference data points X, Y, and Z coordinates and plotting each one of the plurality of difference data points to produce a three-dimensional representation.

10. A method as set forth in claim 1 and further comprising assigning to each one of the plurality of difference data points X, Y, and Z coordinates and scaling the Z coordinate to a zero value to generate a two-dimensional colored density diagram of the alternans data.

11. A method as set forth in claim 1 and further comprising assessing the quality of the alternans data using detected trends in the alternans data.

12. A method as set forth in claim 11 and further comprising providing an input for manual correction of the alternans data.

13. An apparatus for displaying alternans data of an electrocardiogram signal, the electrocardiogram signal having a plurality of odd beats and a plurality of even beats, the apparatus comprising:

a display; and a processor that produces a representation of the alternans data, the processor calculating an odd median complex for at least one of the plurality of odd beats, the odd median complex having a plurality of odd data points;

calculating an even median complex for at least one of the plurality of even beats, the even median complex having a plurality of even data points;

comparing the plurality of odd data points with the plurality of even data points to obtain a plurality of difference data points;

assigning each one of the plurality of difference data points a color corresponding to an amplitude;

displaying the plurality of difference data points as a difference curve on the display; and generating a plurality of difference curves and displaying the plurality of difference curves on the display in a temporal alignment.

14. An apparatus as set forth in claim 13, wherein the processor displays at least one indicator corresponding to at least one portion of the alternans data.

15. An apparatus as set forth in claim 14, wherein the at least one indicator includes a QRS-end indicator.

16. An apparatus as set forth in claim 14, wherein the at least one indicator includes a Tend indicator.

17. An apparatus as set forth in claim 13 wherein the display is one of a black and white display capable of displaying a plurality of shades of gray and a red-blue-green color display capable of displaying true colors.

18. An apparatus for displaying T-wave alternans data from an electrocardiogram, the apparatus comprising:

a display; and means for producing a spatiotemporal representation of the T-wave alternans data on the display, wherein the producing means are configured to compare a plurality of odd data points with a plurality of even data points corresponding to the T-wave alternans data to obtain a plurality of difference points, and configured to display the plurality of difference points as a difference curve.

19. A method of quantifying alternation in an electrocardiogram signal having a plurality of beats, the method comprising:

receiving digitized electrocardiogram data representing the electrocardiogram signal;

calculating odd median complexes for odd beats in the electrocardiogram data;

calculating even median complexes for even beats in the electrocardiogram data; comparing the odd median complexes with the even median complexes to obtain estimates of the amplitude of beat-to-beat alternation in the electrocardiogram signal; generating difference curves from the estimates of the amplitude of beat-to-beat alternation; and displaying the difference curves as a spatiotemporal representation of the beat-to-beat alternation in the electrocardiogram signal.

20. A method as set forth in claim 19 and further comprising obtaining absolute difference estimates of the amplitude of beat-to-beat alternation in the electrocardiogram signal.

21. A method as set forth in claim 19 and further comprising distinguishing between alternans distribution and artifact distribution.

22. A method as set forth in claim 19 and further comprising displaying the difference curves in a temporal alignment as a two-dimensional representation.

23. A method as set forth in claim 19 and further comprising displaying the difference curves in a temporal alignment as a three-dimensional representation.

24. A method as set forth in claim 19 and further comprising assigning a true color to each one of the estimates of the amplitude of beat-to-beat alternation.

25. A method as set forth in claim 19 and further comprising assigning a shade of gray to each one of the estimates of the amplitude of beat-to-beat alternation.

26. A method as set forth in claim 19 and further comprising assigning to each one of the estimates X and Y coordinates and plotting the estimates to produce a two-dimensional representation.

27. A method as set forth in claim 19 and further comprising assigning to each one of the estimates X, Y, and Z coordinates and plotting the estimates to produce a three-dimensional representation.

28. A method as set forth in claim 19 and further comprising assigning to each one of the estimates X, Y, and Z coordinates and scaling the Z coordinate to a zero value to generate a two-dimensional colored density diagram.

29. A method as set forth in claim 19 and further comprising providing an input for manual correction of the alternans data.

\* \* \* \* \*